United States Patent [19]

Albert et al.

[11] Patent Number: 5,025,794
[45] Date of Patent: Jun. 25, 1991

[54] METHOD FOR ANALYSIS OF ELECTROCARDIOGRAPHIC SIGNAL QRS COMPLEX

[75] Inventors: David E. Albert; Edward J. Berbari, both of Edmond, Okla.

[73] Assignee: Corazonix Corporation, Oklahoma City, Okla.

[21] Appl. No.: 238,503

[22] Filed: Aug. 30, 1988

[51] Int. Cl.⁵ .......................................... A61B 5/04
[52] U.S. Cl. ............................... 128/696; 364/413.06
[58] Field of Search ............... 128/696, 702, 705, 710; 364/413.06

[56] References Cited

U.S. PATENT DOCUMENTS 4,458,691  7/1984  Netravali ......................... 128/705
4,630,204 12/1986  Mortara ........................... 128/696
4,680,708  7/1987  Ambos et al. .................... 128/702
4,732,158  3/1988  Sadeh .............................. 128/702

Primary Examiner—William E. Kamm
Attorney, Agent, or Firm—Laney, Dougherty, Hessin & Beavers

[57] ABSTRACT

A method and apparatus for examining the QRS complex of ECG signals to detect minute late potentials. The system functions to filter the QRS signals bi-directionally, and further separately processes the two filtered signals through selected window functions before summation. The summed signal is then passed through a smoothing function to produce an output signal of ideal phase that delineates any late potentials within the QRS complex.

10 Claims, 3 Drawing Sheets

METHOD FOR ANALYSIS OF ELECTROCARDIOGRAPHIC SIGNAL QRS COMPLEX

BACKGROUND OF THE INVENTION

1. Field of the Invention

The invention relates generally to a computer implemented process for examination of the QRS complex of an electrocardiograph signal in order to predict the likelihood of arrhythmic tachycardia.

2. Description of the Prior Art

It was early recognized that a diseased state in the myocardium will alter the conduction velocity of electrical energy; however, these late potentials showing up in the QRS signal are very small and require specialized data acquisition techniques in order to be detected and measured. It is not possible to examine such low power signals using conventional ECG equipment and, in general, two techniques for high resolution electrocardiography (HRECG) had been available to look at such signals: these were (1) signal averaging and (2) high gain ECG. Signal averaging relies on the fact that the noise in the signal is random, therefore the addition of a large number of signals of like time frame will result in noise cancellation. The latter technique uses very high gain amplifiers and extensive shielding to reduce the amount of noise in the signal, thereby extracting the signals by brute force. The further refinements in detection circuitry have taken the form of various filtering schemes effective to further delineate the late potential indications.

The basic and earliest disclosure of the present form of heart attack prediction method was made by Berbari et al. entitled "Non-Invasive Detection of Delayed Ventricular Activation Presaging Arrythmias", in *Circulation*, Vols. 59 and 60, Supp. II, October, 1977, Abstract No. 347, page 111-91. This Abstract was soon followed by a publication in *The American Journal of Cardiology*, Volume 41, page 697-701, April, 1978, entitled "Recording from the Body Surface of Arrythmogenic Ventricular Activity During the S-T Segment-"—Berbari et al. This subject was also extensively investigated in the doctoral thesis of Edward J. Berbari entitled "New Engineering Approaches to Non-Invasive HIS-Purkinje System Recordings" as submitted to the University of Iowa in May of 1980. These prior studies were concerned with signal processing and the manner in which the electrocardiograph (ECG) QRS complex may be best filtered with minimum phase shift thereby to remove all but the usable minute voltage indications which convey the indication of ventricular tachycardia.

Another important early contribution to filtering of the QRS complex of the ECG signal is found in the British patent no. 1,556,512, earlier filed in Japan by the Japanese corporation Fukuda Denshi Co., Ltd. in December 1975. This patent recognized the difficulties in refinement of cardiographic signals and sought better forms of filter for eliminating unwanted fluctuating components. This teaching attempted filtering with analog filters and the attendant problems with phase shift and ringing. The method evolved was termed on-line time reversal filtering wherein the input signal is passed through two analog filters in forward and reverse time order and then combined to produce a signal that is relatively free of phase distortion. This method of filtering is further pursued in specific relation to electrocardiogram processing in a work entitled "Linear Phase Filtering—A New Approach to Distortion-Free Electrocardiograms"—by David Tayler et al., as published in *Transactions of IEEE*, 1985. A similar teaching is contained in *IEEE Transactions on Accoustics, Speech, and Signal Processing* of October 1974, Vol. 22, No. 5, page 384, in an article entitled "Two-Pass Recursive Digital Filter with Zero Phase Shift"—by J.J. Kormylo and V.K. Jain. This teaching is directed to elimination of phase distortion by a two-pass scheme where the signal is processed in both the causal and the reverse causal directions.

Yet another pertinent teaching relative to examination of the QRS complex of the ECG is set forth in U.S. Pat. No. 4,422,459 in the name of Simson as issued on Dec. 27, 1983. This patent teaches the filtering of each sample point of the QRS complex signal only once; however, a selected front portion of the QRS complex is filtered in the forward direction while the remaining latter portion of the QRS is filtered in the reverse direction. This is yet another approach to the filtering of the signal averaged QRS complex. This approach was also generally discussed in an article by Simson entitled "Use of Signals in Determining QRS Complex to Identify Patients with Ventricular Tachycardia After Myocardial Infarction" as published in *Circulation*, Volume 64, No. 2, August 1981 at pages 235-241.

SUMMARY OF THE INVENTION

The present invention relates to a method and apparatus for analysis of the late potential portion of the QRS complex of an electrocardiograph (ECG) signal. The selected portion of the ECG signal is time averaged over a selected duration whereupon either the X, Y, Z or vector signals are further analyzed to isolate anomalies in the late potentials of the QRS complex. Further analysis may be selected from a filtering option which includes a uni-directional or bi-directional butterworth-type filter, a finite impulse response filter or a least squares fit filter, and the system is capable of further refinement using a window function in the form of a fast Fourier transform generating frequency domain indications of the QRS late potentials.

Therefore, it is an object of the present invention to provide in an electrocardiogram analysis process a procedure for further refinement of late potentials indicative of heart disease.

It is also an object of the invention to provide an automated process that produces a much improved indication of signal anomaly.

It is yet further an object of the present invention to provide a non-invasive method for producing clear and reliable indication of cardiac problems.

Finally, it is an object of the invention to provide method and apparatus that is program controlled for easy operation by the skilled technician to measure cardiac late potentials with precision and reliability.

Other objects and advantages of the invention will be evident from the following detailed description when read in conjunction with the accompanying drawings which illustrate the invention.

DETAILED DESCRIPTION OF THE INVENTION

Figure 1:
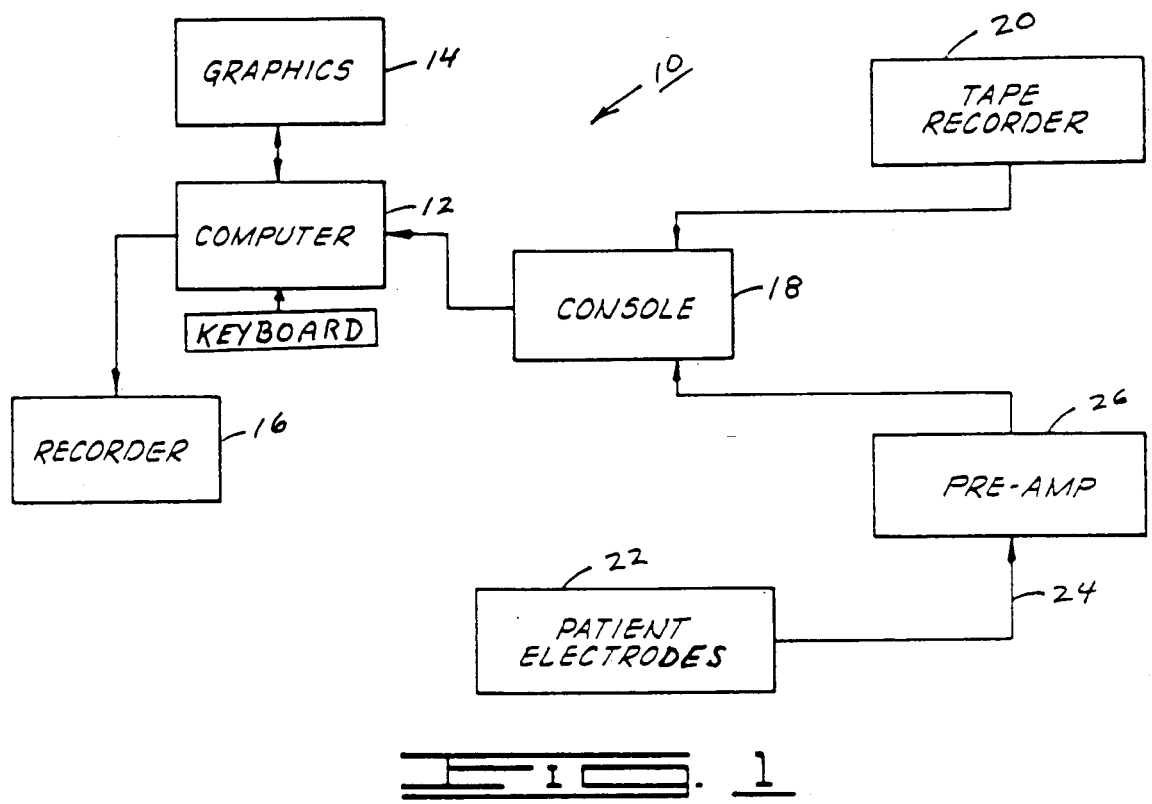
FIG. 1 is a block diagram of a computer controlled system that utilizes the present invention.

FIG. 1 illustrates the basic interactive components of a signal averaging ECG system 10. The system 10 is an integrated signal averaging electrocardiograph which is portable for noninvasive use to determine a great number of effects and analyses that may show up in the heart beat signal. It should be understood that the overall system 10 and software program form no part of the present invention, with the exception of the ECG late potential filtering and analysis components to be more fully described hereinafter.

The computer 12 including graphics screen 14 may be an IBM type PC/AT or clone, or the COMPAQ III. The computer utilizes an 80286 microprocessor with high resolution graphics and it has an 80287 math co-processor. Thirty megabytes of hard disc storage are included along with a 16 bit, 8 channel analog to digital converter. Computer 12 provides output to a recorder 16 which may be any of several types of tape recorder or disc, but which preferably also includes an 8 pen color plotter for recording of patient data.

A console 18 generates control input to the computer 12 and may include the QRS detection hardware, amplifiers and filters for patient input and high level outputs. High level inputs of pre-recorded data from such as an FM tape recorder 20 are optional. The patient electrodes 22, that is the standard form of multiple ECG inputs, are conducted via a cable 24 for indivi dual amplification in a pre-amplifier 26 and the pre-amp outputs are applied to console 18. The pre-amplifier 26 is easily portable and defibrilation protected to provide three high gain, low noise differential channels.

The computer software facilitates the use of the system in simple, interactive manner. Data collection, data storage, file manipulation, and data analysis are performed from within the software, requiring little interaction with the computer's disc operating system. The system 10 is designed to provide the physician with an extremely flexible tool for the acquisition and analysis of ECG late potentials.

The data acquisition facilities provide for real-time input from patient electrodes 22 or high level inputs from tape recorder 20. Real-time input is acquired from either three bipolar body surface ECG leads (electrodes 22), i.e., an orthogonal X, Y, Z configuration, or from 1-3 channels of high-level input from an alternative source such as tape recorder 20. Analog signals are amplified, filtered and sampled by the computer 12. During real-time data collection, a hardware QRS detector and software correlation are employed to select only the signals desired for the average. This data is then saved in a data file on the computer's hard disc for subsequent analysis. The analysis software allows the user to implement any number of the current late potential analysis techniques as reported in the literature. Analysis is menu driven and has print and plot routines for all graphic screens. Signal averaging as carried out to aid in distinguishing late potentials as random noise is inherently eliminated in the averaging process while valid late potential signals are enhanced. Each incoming QRS complex is transferred to the computer, which checks the uniformity of the beat, lines it up with the old average, adds each new point to the average, and increments the total number of beats. In this way a signal average is built up over time. When the user saves a data file, this array of averaged points is saved along with the number of beats and other acquisition parameters. The averaging procedure is extremely effective in reducing noise and, for a 200 beat sample, the signal-to-noise ratio can be improved by as much as 23 db.

Figure 2:
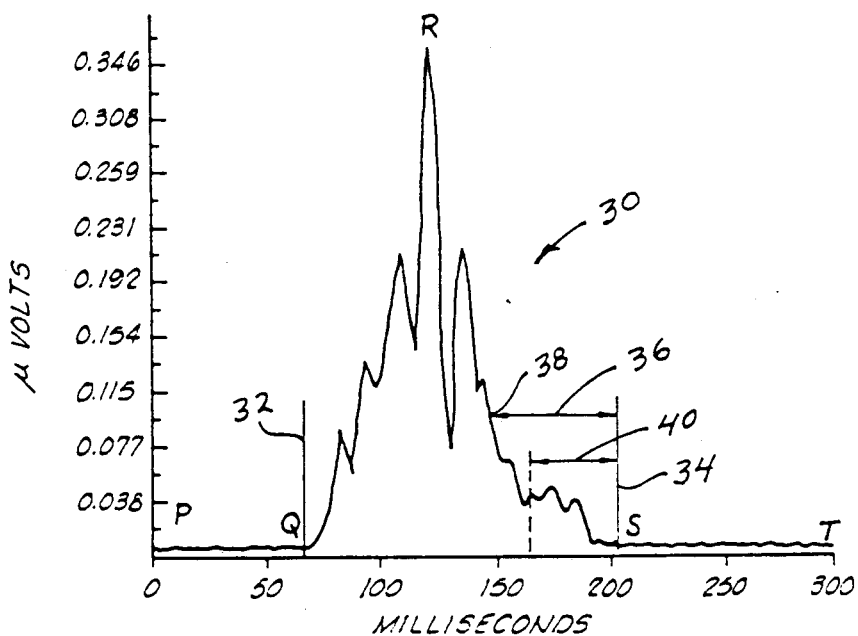
FIG. 2 is a graph in microvolts versus milliseconds illustrating a cardiogram vector for a signal averaged and highpass filtered heart beat.

The system 10 having many digital signal processing capabilities, incorporates three families of signal processing techniques; that is, filtering, Fourier processing (frequency domain), and vector analyses. Vector processing is one of the oldest techniques. This form of processing combines the orthogonal X, Y and Z ECG signals to compile a vector magnitude, i.e., combining all three coordinate inputs into a single vector output as shown in FIG. 2. Thus, the vector output 30 is derived by squaring each of the X, Y and Z signal values and taking the square root of their sum. This is carried out digitally for each sample point along the time axis of the signals.

As shown in FIG. 2, the curve defines the QRS complex in relation to the overall beat (PQRST). The software of the present process automically defines the QRS "ON" bar 32 and the QRS "OFF" bar 34 to set off the QRS complex, and the low amplitude signal portion is defined by arrow 36 as it extends from QRS "OFF" bar 34 to what is defined as the point 38 on the downside slope from the R point in the complex where the vector voltage exceeds the low amplitude signals (LAS). The last 40 milliseconds of the QRS complex is designated as the terminal QRS 40, the selected default value in the program of system 10. This terminal period 40, usually but not always so designated as 40 milliseconds, defines a period during which several late potential parameters may appear.

Filtering is a standard digital signal processing task and, as mentioned in the prior art references, many different attempts at filtering, both analog and digital, have been attempted in the past. The crux of the present invention as carried out by the system 10 is the method of filtering the X, Y and Z ECG signals after signal averaging, and the manner in which all data points are bidirectionally processed to derive an output signal having no phase or impulse response distortion. These filtered QRS complex signals may then be further subjected to fast Fourier transform to provide a frequency analysis of the signal. This overall process is described below and shown in FIG. 3.

The fast Fourier Transform (FFT) is used to numerically calculate the frequency content of a signal. The FFT is a useful analysis tool for determining in what frequency bands signals reside. Once this determination is made, it is possible to use the FFT as a tool simply for a quantitative assessment of the signal presence. In most cases it is possible to differentiate between the spectrum of low level signals and the spectrum of the noise.

Figure 3:
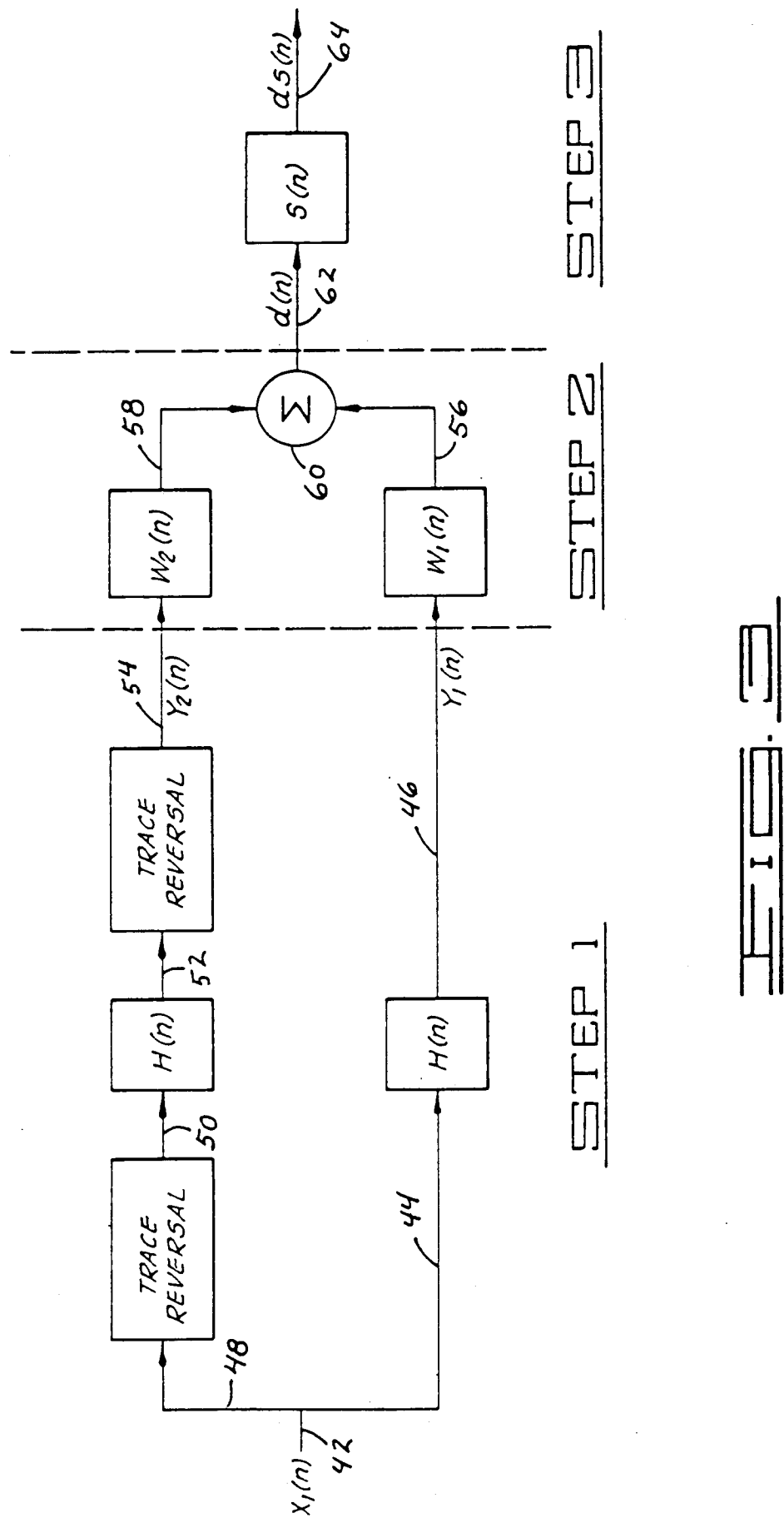
FIG. 3 is a flow diagram of the filtering technique utilized in the present invention.

In FIG. 3, input to the filtering process in the form of a signal $x_1(n)$ may consist of such as signal averaged X, Y and Z ECG signals. The input signal $x_1(n)$ is applied on line 44 to a filter function $H(n)$ which provides output on line 46 of a function $y_1(n)$, and a parallel branch 48 is applied through a trace reversal process. The reversed trace is then applied on line 50 through a filter function H(n) which, in turn, is applied via line 52 through yet another trace reversal procedure to produce a signal y₂(n) on line 54. This completes digital filtering as carried out under software direction in the step 1 phase of the method. This portion of the signal filtering is carried out using infinite impulse response (IIR) digital filters and such practice is more fully described in *Theory and Application of Digital Signal Processing* by Rabiner and Gold, Prentice-Hall Inc. 1975, chapter 4, pages 205–209.

The filter function H(n) is controlled by the software and may take various forms. The filter is selected as one of high pass, low pass or bandpass as the cutoff and/or rolloff limits of each is designated by software selection. Such digital filters can be tailored within a wide range of variables to fit the exigencies of particular applications. It is also contemplated that infinite impulse response (IIR) filter may be employed only in the reversed order processing while finite impulse response (FIR) filtering is applied to normal time procedures.

Signal refinement is then further effected by the application of window functions. The straight-through signal $y_1(n)$ is applied through a window function $W_1(n)$ as output on line 56, and the similar $y_2(n)$ signal on line 54 is applied through a window function $W_2(n)$ as present on line 58. These window function outputs on lines 56 and 58 are then applied to a summation procedure 60 to develop signal d(n), thus completing step 2 of the process. Finally, step 3 consists of applying the signal on line 62 through a polynomial smoothing function S(n) to finally output the smoothed output $d_s(n)$ on line 64.

The program calls for a series of procedures and/or calculations for developing the smoothed output. Step 1 functions to process the filtered signals in forward and reverse time, i.e., with all data points operated on twice.

$$x_1(n) \rightarrow H(n) \rightarrow y_1(n) \quad (1)$$

$$x_1(n) \rightarrow \text{Trace Reverse} \rightarrow x_1{''}(n)$$

$$x_1{''}(n) \rightarrow H(n) \rightarrow y_1{''}(n) \rightarrow \text{Trace Reverse} \rightarrow y_2(n)$$

for n = 1 to N, N = total points.

where
$x_1(n)$ = digitized time, signal of interest,
$x_1{''}(n)$ = time reversal of $x_1(n)$,
H(n) = filter transfer function,
$y_1(n)$ = output of filter in normal time,
$y_1{''}(n)$ = output of filter, time reversed, and
$y_2(n)$ = normal time sense output of re-reverse filter.

Step 2 functions to obtain a display buffer from the signals $y_1(n)$ and $y_2(n)$ utilizing selected window functions. This proceeds as:

$$d(n) = W_1(n)y_1(n) + W_2(n)y_2(n) \quad (2)$$

where
d(n) = display buffer $$W_1(n) = 1 \text{ for } n = 1 \text{ to } HF$$
$$= 0 \text{ for } n = HF + 1 \text{ to } N$$

-continued
$$W_2(n) = 0 \text{ for } n = 1 \text{ to } HF$$
$$= 1 \text{ for } n = HF + 1 \text{ to } N$$

and HF equals the hardware fiducial point adjusted by maximum correlation coefficient. The fiducial point is the location in the display window that is aligned with the QRS signal and the point is chosen by the operator in accordance with display of the desired area. For the horizontal division of 600 points, the normal or default fiducial point position is 200, as similarly shown in the FIG. 2 graph.

The step 3 functions to join any discontinuity of d(n) around the fiducial point HF by a process of polynomial smoothing in accordance with the following:

$$d(n) = d(n) \text{ for } n = 1 \text{ to } HF - 2$$

$$d(n) = d(n) \text{ for } n = HF + 2 \text{ to } N$$

in the relationships $$d(HF - 2) = \frac{d(HF - 3) + d(HF - 2) + d(HF - 1)}{3} \quad (3)$$

$$d(HF - 1) = \frac{d(HF - 2) + d(HF - 1) + d(HF)}{3}$$

$$d(HF) = \frac{d(HF - 1) + d(HF) + d(HF + 1)}{3}$$

$$d(HF + 1) = \frac{d(HF) + d(HF + 1) + d(HF + 2)}{3}$$

$$d(HF + 2) = \frac{d(HF + 1) + d(HF + 2) + d(HF + 3)}{3}$$

where $d(n) \rightarrow S(n) \rightarrow d_s(n)$.

Figure 4:
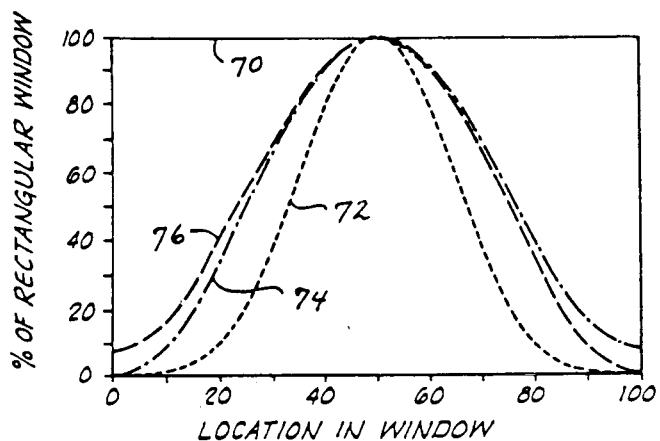
FIG. 4 is a graph illustrating time domain window functions as utilized in the present invention.

The window functions are also used in the fast Fourier Transform process, which in this case is implemented with a "chirp Z" algorithm, and the operator may select from a number of spectral windows. Four of the common FFT windows are available in present programming for the spectral analysis and these are shown graphically in FIG. 4. Thus, the rectangular window 70 is shown extending across points 0–100 with sharp cut-off. By comparison, the window 72 is a more narrow window function known as the Blackman-Harris while the window functions 74 and 76, known as the Hanning and Hamming, respectively, are also available for selection from the protocol menu of the computer 12. The rectangular spectral window 70 is the default window and offers the best spectral resolution, but the lowest signal-to-noise ratio. The remaining windows 72–76 offer varying degrees of performance under specific signal conditions and, generally, these functions trade off frequency resolution for improved signal detection. For example, the Blackman-Harris window function is designed for differentiating two closely spaced harmonics with significantly different amplitudes.

Figure 5A:
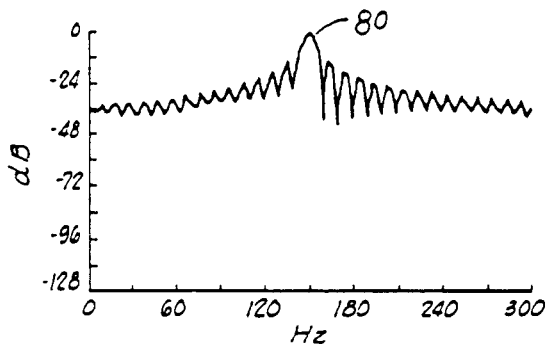
FIGS. 5A, 5B, 5C and 5D are graphs illustrating the frequency effects of the four different windows of FIG. 4.
Figure 5B:
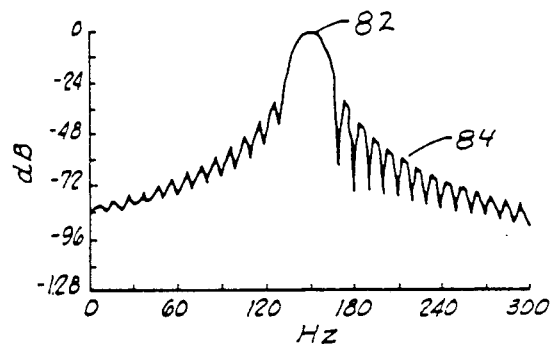
Figure 5C:
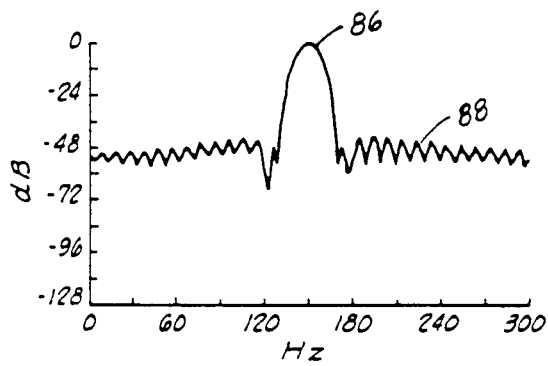
Figure 5D:
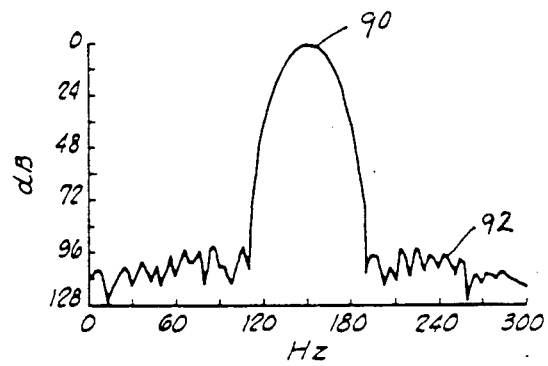

FIGS. 5A–5D illustrate the frequency relationships of the several FFT windows. In FIG. 5A, the rectangular window, the spike or main lobe 70 has a width of about 7.5 Hertz with the base widening slightly but smoothly as amplitude decreases. In FIG. 5B, the Hanning window has a main lobe 82 that is slightly wider and extending side lobes 84 at progressively lower levels. FIG. 5C shows the Hamming window with still wider main lobe 86 yet more controlled side lobes 88, and the Blackman-Harris curve of FIG. 5D shows a much larger, smooth main lobe 90 with very little evidence of side lobing at 92.

The FFT window performance specifications for the subroutine are as follows:

| Type | 6 dB Time-BW Product | Sidelobe Level |
|---|---|---|
| Rectangular | 1.2 | −13 dB |
| Hanning and Hamming | 1.8 | −43 dB |
| Blackman-Harris | 2.1 | −92 dB |

It may be noted from FIG. 5D the manner in which the main lobe 90 approximates the Blackman-Harris values as set forth above for side lobe level and time-bandwidth product. Thus, the effect of this window is to create the same pattern for every frequency component found in the waveform. Each pattern may have a different amplitude, but the resultant spectrum is the sum of all the patterns. If the rectangular window is used (FIG. 5A), the highest frequency resolution is obtained, i.e. the ability to discriminate between two closely spaced components of sufficient amplitude. However, the noise created in the rest of the spectrum may mask over the lower level components. If an alternative window is used, the noise in the spectrum is reduced but the ability to discriminate between closely adjacent components is also reduced. Thus, the operator's choice of the window will depend largely upon the type of analysis desired.

The actual program, subroutine high pass, utilized in the system 10 for carrying out the QRS complex examination is as follows:

```
$include: 'meta.cmn'
C***************************************************************
C
C       Subroutine hipass
C
C       Purpose:  To hipass filter the selected lead using a uni- or
C                 bi-directional Butterworth filter
C
C       Input Variables:
C               -none-
C
C       Output Variables:
C               -none-
C
C       Programmer:   CMH
C       Date:         7/18/87
C
C       This program is Copyright (c), 1987, by Corazonix Corporation,
C       Oklahoma City, Oklahoma.  All Rights Reserved.
C
C*************************************************************** implicit integer*2 (i-n)

$include: 'analysis.cmn' integer*2 m,final
        real pi,c,c1,c2,c3,c4,a,b,d,e,f,outfor(600),outbak(600)
        real b0,b1,b2,b3,b4 data pi/3.14159/,b0/1.0/,b1/2.6131259/,b2/3.4142136/
        data b3/2.6131259/,b4/1.0/

$include: 'cnotice.for'

C
C Determine if unidir(0) or bidir(1)
C
        c=(pi/freq)*hfreq
        c1=sin(c)/cos(c)
        c2=c1*c1
        c3=c1*c2
        c4=c2*c2
```

```
C
C Case of hipass filter order=1, unidir. or bidir.
C
      if(hord .eq. 1)then
            outfor(1)=0.0
            do 100 m=2,600
100               outfor(m)=work(m)-work(m-1)-c1-1.)
     &                    *outfor(m-1))/(1.+c1)
            if(bi .eq.1)then
                  outbak(600)=0.0
                  do 150 m=599,1,-1
150                     outbak(m)=(work(m)-work(m+1)-(c1-1.)*
     &                            outbak(m+1))/(1.+c1)
            endif
C
C Case of hipass filter order=2, unidir. or bidir.
C
      elseif(hord .eq. 2)then
            a=1. + 1.414214 * c1 + c2
            b=1. - 1.414214 * c1 + c2
            d=-2. + c2 * 2.
            outfor(1)=0.0
            outfor(2)=0.0
            do 200 m=3,600
200               outfor(m)=(work(m)-2*work(m-1)+work(m-2)
     &                      -b*outfor(m-2)-d*outfor(m-1))/a
            if(bi .eq. 1)then
                  outbak(600)=0.0
                  outbak(599)=0.0
                  do 250 m=598,1,-1
250                     outbak(m)=(work(m)-2*work(m+1)+work(m+2)
     &                            -b*outbak(m+2)-d*outbak(m+1))/a
            endif
C
C Case of hipass filter order=3, unidir. or bidir.
C
      elseif (hord .eq. 3)then
            a= 1. + (2.*c1) + (2.*c2) + c3
            b=-3. - (2.*c1) + (2.*c2) + (3.*c3)
            d= 3. - (2.*c1) - (2.*c2) + (3.*c3)
            e=-1. + (2.*c1) - (2.*c2) + c3
            outfor(1)=0.0
            outfor(2)=0.0
            outfor(3)=0.0
            do 300 m=4,600
300               outfor(m)=(work(m)-3*work(m-1)+3*work(m-2)
     &              -work(m-3)-b*outfor(m-1)-d*outfor(m-2)-e*outfor(m-3))/a
            if(bi .eq. 1)then
            outbak(600)=0.0
            outbak(599)=0.0
            outbak(598)=0.0
            do 350 m=597,1,-1
350               outbak(m)=work(m)-3*work(m+1)+3*work(m+2)
     &              -work(m+3)-b*outbak(m+1)-d*outbak(m+2)-e*outbak(m+3))/a
            endif
C
C Case of hipass filter order=4, unidir. or bidir.
C
      elseif(hord .eq. 4)then
            c=(pi/freq)*(float(hfreq)/1.24634)
```

```
                c1=sin(c)/cos(c)
                c2=c1*c1
                c3=c1*c2
                a=1. + 1.414214 * c1 + c2
                b=1. - 1.414214 * c1 + c2
                d=-2. + c2 * 2.
                outfor(1)=0.0
                outfor(2)=0.0
                do 400 m=3,600
400                 outfor(m)=(work(m)-2*work(m-1)+work(m-2)
      &                 -b*outfor(m-2)-d*outfor(m-1))/a
                if(bi .eq. 1)then
                    outbak(600)=0.0
                    outbak(599)=0.0
                    do 450 m=598,1,-1
450                     outbak(m)=work(m)-2*work(m+1)+work(m+2)
      &                     -b*outbak(m+2)-d*outbak(m+1))/a
                endif C...            Store outfor in a temporary array
                do 460 j=1,600
460                 work1(j)=outfor(j)

outfor(1)=0.0
                outfor(2)=0.0
                do 470 m=3,600
470                 outfor(m)=(work1(m)-2.*work1(m-1)+work1(m-2)
      &                 -b*outfor(m-2)-d*outfor(m-1))/a
                if(bi .eq. 1)then C...            Store outbak in a temporary array
                    do 475 j=1,600
475                     work1(j)=outbak(j)

outbak(600)=0.0
                    outbak(599)=0.0
                    do 480 m=598,1,-1
480                     outbak(m)=(work1(m)-2*work1(m+1)+work1(m+2)
      &                     -b*outbak(m+2)-d*outbak(m+1))/a
                endif
        endif
C
C Place results in work array and smooth around fidr if bidirectional
C
        if (bi .eq. 0)then
                do 500 m=1,600
500                 work(m)=outfor(m)
        else
                do 525 m=1,fidr
525                 work(m)=outfor(m)
                do 550 m=fidr+1,600
550                 work(m)=outbak(m)

work(fidr)=(work(fidr-1)+work(fidr+1))/2
                work(fidr-1)=(work(fidr-2)+work(fidr))/2
                work(fidr+1)=(work(fidr+2)+work(fidr))/2
        endif
9999    return
        end
```

This subroutine is effective to implement a uni-directional or bi-directional butterworth filter from first order through fourth order and thereafter apply the window function and smoothing to produce the desired output QRS complex information. The program steps for first through fourth order processing are listed in succession as denoted by left column C-C-C through file no. 450 which is then followed by window function processing and smoothing to produce final data.

The foregoing discloses a novel procedure as implemented by digital computer for examining the low amplitude signals of the QRS complex for tell-tale late potentials indicative of ventricular tachycardia and likelihood of cardiac problems. The process utilizes selected combinations of filtering, back and forward, and signal summing with attendant weighting and smoothing to derive reliable indications from otherwise faint or masked late potential signals.

Changes may be made in combination and arrangement of elements or steps as set forth in the specification and shown in the drawings; it being understood that changes may be made in the embodiments disclosed without departing from the spirit and scope of the invention as defined in the following claims.

What is claimed is:

1. A method for determining anomalous late potentials in the QRS complex of an electrocardiographic beat signal, comprising:
    deriving the QRS signal of the beat signal as a series of digital sample values at a selected sample rate;
    filtering the QRS signal sample values through a digital filter of selected pass band;
    filtering the QRS signal sample values in reversed time order through a digital filter of said selected pass band;
    processing each of the filtered QRS signal in accordance with a predetermined window function and summing the resulting signal to produce a QRS summation signal; and
    smoothing the QRS summation signal to produce a QRS signal replica accentuating the non-random late potential signal components within the QRS low amplitude signal sector.

2. A method as set forth in claim 1 wherein the steps of filtering each include:
    selecting a filter that is a low pass type.

3. A method as set forth in claim 1 wherein the steps of filtering each include:
    selecting a filter that is a highpass type.

4. A method as set forth in claim 1 wherein the steps of filtering each include:
    selecting a filter that is a fourth order Butterworth type.

5. A method as set forth in claim 4 wherein:
    said QRS signal is derived from a selected one of the X, Y and Z electrocardiographic responses and averaged over a selected duration.

6. A method as set forth in claim 1 wherein:
    said window function is a rectangular type.

7. A method as set forth in claim 1 wherein:
    said window function is a Blackman-Harris type.

8. A method as set forth in claim 1 wherein:
    said window function is a Hanning type.

9. A method as set forth in claim 1 wherein:
    said window function is a Hamming type.

10. A method as set forth in claim 1 wherein:
    said QRS signal is derived from a selected one of the X, Y and Z electrocardiographic responses and averaged over a selected duration.

* * * * *